United States Patent [19]

Carter

[11] Patent Number: 5,166,066
[45] Date of Patent: Nov. 24, 1992

[54] TRANSFORMED CELLS COMPRISING GABA$_A$ RECEPTORS

[75] Inventor: Donald B. Carter, Kalamazoo, Mich.

[73] Assignee: The Upjohn Company, Kalamazoo, Mich.

[21] Appl. No.: 728,218

[22] Filed: Jul. 11, 1991

[51] Int. Cl.$^5$ .................. C12N 5/00; C12N 15/00
[52] U.S. Cl. .................. 435/240.2; 435/69.1; 530/350; 530/395; 935/70
[58] Field of Search ............... 530/395, 250; 435/69.1, 435/240.2, 91; 536/27

[56] References Cited

PUBLICATIONS

Aiello, et al. Vinology 94:460-469 1979.
Chen, et al. MCB 7:2745-2752 1987.
Puia et al. PNAS 86:7275-7279 1989.
Pritchett et al., J. Neurochemistry 54:1802-1804 1990.
Luddins et al., Nature 346:648-651 1990.
Moss, S. J. et al., "Cloned GABA receptors are maintained in a stable cell line: allosteric and channel properties," Eur. J. Pharmacol.-Molec. Pharmacol. Section 189:77-88 (1990).
Malherbe, P., et al., "Functional Characteristics and Sites of Gene Expression of the $\alpha_1,\beta_1,\gamma_2$-Isoform of the Rat GABA$_A$ Receptor," J. Neurosci. 10(7):2330-2337 (1990).
Ymer, S., et al., "Structural and functional characterization of the $\gamma_1$ subunit of GABA$_A$/benzodiazepine receptors," The EMBO J. 9(10):3261-3267 (1990).
Lüddens, H. and W. Wisden, "Function and pharmacology of multiple GABA$_A$ receptor subunits," TiPS 12:49-51 (1991).
Knapp, R. J., et al., "From Binding Studies to the Molecular Biology of GABA Receptors," Neurochemical Research 15(2):105-112 (1990).
Olsen, R. W., et al., "Molecular biology of GABA$_A$ receptors," FASEB J. 4:1469-1480 (1990).
Mohler, H., et al., "GABA$_A$-Receptors: Structural Requirements and Sites of Gene Expression in Mammalian Brain," Neurochemical Research 15(2):199-207 (1990).
F. Anne Stephenson, "Understanding the GABA$_A$ receptor: a chemically gated ion channel," Biochem. J. 249:21-32 (1988).
Barnard, E. A., et al., "Molecular biology of the GABA$_A$ receptor: the receptor/channel superfamily," TINS 10(12):502-509 (1987).
Schofield, P. R., et al., "Sequence and functional expression the GABA$_A$ receptor shows a ligand-gated receptor super-family," Nature 328:221-227 (1987).
Levitan, E. S., et al., "Structural and functional basis for GABA$_A$ receptor heterogeneity," Nature 335:76-79 (1988).
Schofield, P. R., et al., "Sequence and expression of human GABA$_A$ receptor $\alpha$1 and $\beta$1 subunits," FEBS 244(2):361-364 (1989).
Pritchett, D. B., et al., "Importance of a novel GABA$_A$ receptor subunit for benzodiazepine pharmacology," Nature 338:582-585 (1989).
Ymer, S., et al., "GABA$_A$ receptor $\beta$ subunit heterogeneity: functional expression of cloned cDNAs," The EMBO Journal 8(6):1665-1670 (1989).
Pritchett, D. B. et al., "Type I and Type II GABA$_A$--Benzodiazepine Receptors Produced in Transfected Cells," Science 245:1389-1392 (1989).
Shivers, B. D., et al., "Two Novel GABA$_A$ Receptor Subunits Exist in Distinct Neuronal Subpopulations," Neuron 3:327-337 (1989).
Ymer, S., et al., "Sequence and expression of a novel GABA$_A$ receptor $\alpha$ subunit," FEBS 258(1):119-122 (1989);.

Primary Examiner—John J. Doll
Assistant Examiner—Donald E. Adams
Attorney, Agent, or Firm—Mark DeLuca

[57] ABSTRACT

A stable transformed HEK 293 cell comprising a functional GABA$_A$ receptor that comprises a GABA$_A$ receptor $\alpha$ subunit, a GABA$_A$ receptor $\beta$ subunit and a GABA$_A$ receptor $\gamma$ subunit is disclosed.

20 Claims, No Drawings

TRANSFORMED CELLS COMPRISING GABA$_A$ RECEPTORS

FIELD OF THE INVENTION

The present invention relates to stable transformed eukaryotic cells which produce functional GABA$_A$ receptors that include a benzodiazepine binding site.

BACKGROUND OF THE INVENTION $\gamma$-Aminobutyric acid (GABA) is the major inhibitory neurotransmitter in the mammalian central nervous system. The major type of receptor for the inhibitory neurotransmitter $\gamma$-aminobutyric acid (GABA), called the GABA$_A$ receptor, is a member of a gene superfamily of ligand-gated ion channels. GABA, the endogenous ligand for the GABA$_A$-complex, stimulates chloride ion conductance through the associated chloride ion channel. The predominant effect of GABA is the interaction with a specific receptor protein which results in an increase of the chloride ion conductance of the post-synaptic membrane to produce an inhibition of neuronal firing.

The GABA$_A$ receptor is a multi-subunit ligand-gated ion channel. This receptor is a heterooligomeric protein composed of several distinct polypeptide types. Four different classes of subunit have been defined; $\alpha$, $\beta$, $\gamma$, and $\delta$. Multiple variants within these classes exist. Sequences of seven $\alpha$, three $\beta$, two $\gamma$ and one $\delta$ subunits have been reported. Molecular cloning of these polypeptides reveals that they show 20-40% identity with each other, and 10-20% identity with polypeptides of the nicotinic acetylcholine receptors and strychnine-sensitive glycine receptor. Each polypeptide type is also represented by a family of genes whose members have 60-80% amino acid sequence identity. Regions of conserved and variable amino acid sequence suggest structural and functional domains within each polypeptide. All of the polypeptides when expressed in heterologous cells produce GABA-activated chloride channels, and the different subtypes express different pharmacological properties. The distributions of mRNAs for the different GABA$_A$ receptor polypeptides and their subtypes show significant brain regional variation consistent with pharmacological and biochemical evidence for receptor heterogeneity. Subpopulations of GABA$_A$ receptors with different cellular and regional locations show differential sensitivity to GABA, to modulators like steroids, to physiological regulation, to disease processes, and to pharmacological manipulation by drugs such as benzodiazepines. The properties of the different subpopulations of GABA$_A$ receptors are determined by which of the one or more different polypeptides and their subtypes are expressed in a given cell to produce a variety of different oligomeric protein structures.

The GABA$_A$-receptor chloride-ionophore complex (GABA$_A$-complex) is the primary site of action for many of the drugs used to treat anxiety and seizure disorders such as the benzodiazepines and anticonvulsant barbiturates. By allosteric drug-induced modulation the receptors serve as molecular control elements through which the levels of anxiety, vigilance, muscle tension and epileptiform activity can be regulated. The allosteric modulation of the GABA$_A$ receptor by different agents acting at independent sites on the GABA$_A$-complex can be demonstrated by a variety of methods including electrophysiological measurements with intact cells and isolated membrane fragments (e.g. patch clamp preparations), radioligand binding studies using tissue homogenates, and by $^{36}$Cl-flux measurements using tissue slices, cultured neurons, and cell free membrane vesicle preparations.

There is a need for a stable in vitro system useful to identify and characterize compounds that have GABA$_A$ receptor binding properties and activities similar to those of the known active benzodiazepine compounds. According to the present invention, stable permanent lines of transformed host cells are provided which contain GABA$_A$ receptors that bind to benzodiazepines. These cells lines can be useful to identify compounds with activities similar to those of the known benzodiazepines using patch clamp preparations as well as the other methods available to observe receptor activity. The stable permanent cell lines can be cultured to provide a consistent laboratory research model.

INFORMATION DISCLOSURE

Schofield, P. R. et al. Nature 328:221-227 (Jul. 16, 1987) disclose that amino-acid sequences derived from cDNAs encoding $\alpha$- and $\beta$-subunits of the GABA$_A$ receptor from bovine brain show homology to other ligand-gated receptor subunits. A functional receptor and ion channel with the pharmacological properties characteristic of the GABA$_A$ receptor is disclosed. This functional receptor was produced by the co-expression of the in vitro generated $\alpha$- and $\beta$-subunit RNAs in Xenopus oocytes.

Levitan, E. S., et al. Nature 335:76-79 (Sep. 1, 1988) disclose cDNAs encoding two additional GABA receptor $\alpha$-subunits. The reported variation in $\alpha$-subunits confirmed that the receptor is heterogenous. The $\alpha$-subunits disclosed are differentially expressed within the central nervous system. Receptor subtypes transiently produced in Xenopus oocytes by the differential expression of $\alpha$-subunits with a $\beta$-subunit can be distinguished by the parent sensitivity to GABA.

Schofield, P. R., et al. FEBS 244-Lett(2):361-364 (February 1989) disclose the amino-acid sequences of human GABA$_A$ receptor $\alpha_1$ and $\beta_1$ subunits. The cloned human GABA$_A$ receptor subunits induce the formation of GABA-gated chloride channels when transiently expressed in mammalian cells.

Pritchett, D. B., et al. Nature 338:582-585 (Apr. 13, 1989) disclose a cloned cDNA encoding a new GABA$_A$ receptor subunit termed $\gamma_2$, which has approximately 40% sequence identity with $\alpha$ and $\beta$ subunits. The mRNAs are prominently localized in neural subpopulations throughout the central nervous system. It is reported that when transiently expressed in human cells the co-expression of the $\gamma_2$ subunit with $\alpha_1$ and $\beta_1$ subunits produces GABA$_A$ receptors displaying high affinity binding for central benzodiazepine receptor ligands. In the absence of the $\gamma_2$ subunit, GABA$_A$ receptors whose primary structure is comprised of $\alpha$ and $\beta$-subunits, lack binding sites for benzodiazepines.

Ymer, S., et al. EMBO J. 8(6):1665-1670 (1989) disclose cloned cDNAs encoding two new $\beta$-subunits of rat and bovine GABA$_A$ receptor. The new receptors termed $\beta_2$ and $\beta_3$ share approximately 72% sequence identity with the previously characterized $\beta_1$ polypeptide. Each $\beta$-subunit when co-expressed in Xenopus oocytes with an $\alpha$-subunit form functional GABA$_A$ receptors.

Pritchett, D. B., et al. Science 245:1389-1392 (Sep. 22, 1989) disclose GABA$_A$ receptors assembled from one of three different α-subunits ($α_a$, $α_2$ or $α_3$) in combination with a $β_1$ and a $γ_2$-subunit and transiently expressed in mammalian cells display the pharmacological properties of either type 1 or type 2 receptor subtypes. Accordingly, when transiently expressed in mammalian cells each of the three combinations form $GABA_A$ receptors which bind to benzodiazepines. Receptors containing the $α_3$ subunits show a greater GABA potentiation of benzodiazepine binding than receptors containing the $α_1$ or $α_2$ subunit.

Shivers, B. D., et al., Neuron 3:327–337 (September 1989) disclose two cDNAs encoding novel $GABA_A$ receptor subunits isolated from rat brain library. These subunits, $γ_2$ and $δ$ share approximately 35% sequence identity with $α$ and $β$ subunits and form functional GABA-gated chloride channels when expressed alone in vitro. The $γ_2$ subunit is the rat homolog of the human $γ_2$ subunit.

Ymer, S., et al., FEBS 258-Lett(1):119–122 (November 1989) disclose cloned cDNA encoding the bovine $α_4$ subunit of the $GABA_A$ receptor. The $α_4$ subunit shares 53–56% sequence similarity to the previously characterized $α_1$, $α_2$, and $α_3$ subunits. Co-expression of $α_4$ and $β_1$ in Xenopus oocytes resulted in the formation of a GABA-gated chloride channel with expected pharmacology although no benzodiazepine potentiation was observed.

Pritchett, D. B. and P. H. Seeburg, J. Neurochem. 54(5):1802–1804 (1990) disclose that cDNA encoding a protein with 70% amino acid identity to the previously characterized $GABA_A$ receptor α-subunit was isolated from a rat brain cDNA library. The new subunit, $α_5$, when transiently co-expressed with a $β$ and $β_2$-subunit in cultured cells, produces receptors displaying high affinity binding sites for both a GABA agonist and benzodiazepines.

Moss, S. J., et al. Eur. J. of Pharmacol.—Molec. Pharmacol. Sec. 189:77–88 (1990) disclose that cloned cDNAs encoding $α_1$- and $β_1$-subunits of the bovine brain $GABA_A$ receptor co-transfected using a dexamethasone-inducible promoter into cultured chinese hamster ovary (CHO) cells with selection to form a stable cell line. However, use of a strong constitutive promoter led to cell death upon appearance of receptors at high density. Cells containing the subunits under an inducible promoter expressed receptors which display a high binding affinity to $GABA_A$ receptor agonists, and were potentiated by the barbiturate, pentobarbitone, and was reversibly blocked by bicuculline and picrotoxin but was not enhanced by benzodiazepines. The current responses reported were very small (<50 pA), which may be due to the fact that the CHO cells were not electrically linked.

Malherbe, P., et al. J. Neurosci. 10(7):2330–2337 (July 1990) disclose the cloning of the $β_2$-subunit cDNA of rat brain and its functional analysis by co-expression with $α_1$- and $β_1$-subunits in Xenopus oocytes.

Lüddens, H., et al. Nature 346:648–651 (Aug. 16, 1990) disclose a novel subunit, $α_6$, of cerebellar granular cells. Cultured mammalian cells which transiently expressed subunit cDNAs produced recombinant receptors composed of $α_6$-, $β_2$- and $β_2$-subunits bind with high affinity to the GABA agonist muscimol and the benzodiazepines Ro15-4513 and Ro15-1788 but not to other benzodiazepines.

Ymer, S., et al. EMBO J. 9 (10):3261–3267 disclose a comparison between the $GABA_A$ receptor $γ_1$-subunit of rat, human and bovine origin compared to the $β_2$-subunit in structure and function. Both γ-subunit variants share 74% sequence similarity. When co-expressed with $α$ and $β$ subunits in Xenopus oocytes and transiently co-expressed mammalian cells, the γ variants mediate the potentiation of GABA- evoked currents by benzodiazepines and help generate high affinity binding sites for these drugs.

Lüddens, H. and W. Wisdon, TiPS (February 1991) 12:49–51 refer to function and pharmacology of multiple $GABA_A$ receptor subunits. Alpha subunit heterogeneity, benzodiazepine pharmacology, the role of the other subunits and natural occurring subunit compositions are discussed.

Knapp, R. J. et al., Neurochemical Research (1990) 15(2):105–112 refer to binding studies with and the molecular biology of GABA receptors. A review of binding activities of GABA receptors is provided.

Olsen, R. W. and A. J. Tobin, FASEBJ. (March 1990) 4:1469–1480 refer to the molecular biology of $GABA_A$ receptors. A discussion of the various subtypes of the receptor is provided.

Mohler, H. et al., Neurochemical Research (1990) 15(2):199–207 refer to structural requirements of $GABA_A$ receptors and sites of gene expression in mammalian brain.

Stephenson, F. A., Biochem. J. (1988) 249:21–32 refers to understanding the $GABA_A$ receptor: a chemically gated ion channel. A discussion of the structure, function, diversity and molecular biology of the GABA receptor is provided.

Barnard, E. A., et al., TINS, (1987) 10:(12):502–509 refer to the molecular biology of the $GABA_A$ receptor: the receptor/channel superfamily. A discussion of the diverse subtypes of the GABA receptor is provided.

SUMMARY OF THE INVENTION

The present invention relates to a stable transformed HEK 293 cell comprising a functional $GABA_A$ receptor that comprises a $GABA_A$ receptor α subunit, a $GABA_A$ receptor β subunit and a $GABA_A$ receptor γ subunit.

DETAILED DESCRIPTION OF THE INVENTION

The present invention provides stable cell lines that contain $GABA_A$ receptors containing at least one α-subunit, at least one β-subunit and at least one γ-subunit. The receptors present in cells according to the instant invention function as a benzodiazepine receptor-chloride channel complex. The cell line according to the present invention is stable and permanent which means it can grow in culture and continue through passages or generations to carry and be capable of expressing DNA sequences which encode the $GABA_A$ receptor subunits that form the functional $GABA_A$ receptors. The subunits produced form functional receptors.

Permanent cell lines capable of expressing high levels of function $GABA_A$ receptors are valuable for CNS drug development. The cultured cells expressing a single $GABA_A$ receptor subtype are useful for electrophysiological studies to determine the intrinsic pharmacological activity of a drug candidate on that particular receptor subtype. Alternatively, drugs whose biological activities are known can be used to correlate the intrinsic activity at each receptor subtype with desirable or undesirable biological effects. The use of the permanent cell lines expressing each receptor subtype greatly facilitates the decoding of structure-activity relationships with the various $GABA_A$ receptor subtypes.

According to the present invention, DNA sequences encoding the various receptor subunits are operably linked to expression elements, usually as part of a plasmid, and introduced into human embryonic kidney (HEK) 293 cells. The preferred method of introducing the foreign DNA into the cells is using CaPO$_4$ transfection methods to introduce plasmids containing DNA encoding a receptor subunit. CaPO$_4$ transfection is a widely known technique which one of ordinary skill in the art can readily perform. Other means of DNA insertion such as electroporation, microprojectile bombardment and recombinant viral vector infection are useful to practice the present invention.

Use of HEK 293 cells is desirable because, when grown in culture, they form electrically linked cell clusters which allow for more effective current measurements in path clamp electrical studies. Other cell types which grow in cell clusters and exhibit electrically linked characteristics are also useful in practicing the present invention. Many cell types, however, do not exhibit this type of additive quality which is associated with HEK 293 cell clusters. Prior attempts at constructing cell lines which contain non-naturally occurring functional GABA$_A$ receptors useful as drug targets did not recognize or exploit the advantages of using electrically linked cell clusters. The cell lines created in earlier attempts were not useful in the way that cells according to the present invention are.

Currently, there are seven known $\alpha$ subunits, three known $\beta$ subunits, two known $\gamma$ subunits and one known $\delta$ subunit. The DNA sequence of these twelve known subunits are published and one having ordinary skill in the art could isolate each of these subunits using well known methods. The DNA sequences are reported in the following references:

1) $\alpha_1$ Schofield, P. R., et al. FEBS 244-Lett(2):3-61-364 (February 1989) disclose the amino-acid sequences of human GABA$_A$ receptor $\alpha_1$ and $\beta_{12}$ subunits. Schofield, P. R. et al. Nature 328:221"227 (Jul. 16, 1987) disclose amino-acid sequences derived from cDNAs encoding $\alpha$- and $\beta$-subunits of the GABA$_A$ receptor from bovine brain.

2) $\alpha_2$ Pritchett, D. B. and P. H. Seeburg, J. Neurochem. 54(5):1802-1804 (1990) disclose the amino acid sequences of rat $\alpha_2$ and rat $\alpha_3$.

3) $\alpha_3$ Pritchett, D. B. and P. H. Seeburg, J. Neurochem. 54(5):1802-1804 (1990) disclose the amino acid sequences of rat $\alpha_2$ and rat $\alpha_3$.

4) $\alpha_4$ Ymer, S., et al., FEBS 258-Lett(1):119-122 (November 1989) disclose isolation of cDNA encoding the bovine $\alpha_4$ subunit of the GABA$_A$ receptor and report its predicted amino acid sequence.

5) $\alpha_5$ Pritchett, D. B. and P. H. Seeburg, J. Neurochem. 54(5):1802-1804 (1990) disclose isolation of cDNA encoding a protein with 705 amino acid identity to the previously characterized GABA$_A$ receptor $\alpha$-subunit was isolated from a rat brain cDNA library. The predicted amino acid sequence of the new subunit, $\alpha_5$, is disclosed.

6) $\alpha_6$ Lüddens, H., et al. Nature 346:648-651 (Aug. 16, 1990) disclose a novel subunit, $\alpha_6$, of rat cerebellar granular cells.

7) $\beta_1$ Schofield, P. R., et al. FEBS 244-Lett(2):3-61-364 (February 1989) disclose the amino-acid sequences of human GABA$_A$ receptor $\alpha_1$ and $\beta_1$ subunits.

8) $\beta_2$ Ymer, S., et al. EMBO J. 8(6):1665-1670 (1989) disclose cloned cDNAs encoding two $\beta$-subunits of rat and bovine GABA$_A$ receptor. The receptors termed $\beta_2$ and $\beta_3$.

9) $\beta_3$ Ymer, S., et al. EMBO J. 8(6):1665-1670 (1989) disclose cloned cDNAs encoding two $\beta$-subunits of rat and bovine GABA$_A$ receptor. The receptors termed $\beta_2$ and $\beta_3$.

10) $\gamma_1$ Ymer, S., et al. EMBO J. 9 (10):3261-3267 disclose a comparison between the GABA$_A$ receptor $\gamma_1$-subunit of rat, human and bovine origin compared to the $\gamma_2$-subunit in structure and function.

11) $\gamma_2$ Pritchett, D. B., et al. Nature 338:582-585 (Apr. 13, 1989) disclose a cloned cDNA encoding human GABA$_A$ receptor subunit termed $\gamma_2$. Shivers, B. D., et al., Neuron 3:327-337 (September 1989) disclose two cDNAs encoding novel GABA$_A$ receptor subunits isolated from rat brain library $\gamma_2$ and $\delta$. Malherbe, P., et al. J. Neurosci. 10(7):2330-2337 (July 1990) disclose the cloning of the $\gamma_2$-subunit cDNA of rat brain.

12) $\delta$ Shivers, B. D., et al., Neuron 3:327-337 (September 1989) disclose two cDNAs encoding novel GABA$_A$ receptor subunits isolated from rat brain library, $\gamma_2$ and $\delta$.

The subunits known come from various mammalian species including human, rat and bovine species. The various species derived subunits are closely related in structure and function. The present invention is useful using subunits derived from any mammalian species. Embodiments include HEK 293 cells which express GABA$_A$ receptors made up of rat-derived subunits.

According to the present invention, at least one $\alpha$ subunit, at least one $\beta$ subunit and at least one $\gamma$ subunit make up the functional GABA$_A$ receptors present in the HEK 293 cells. Additional subunits can also be present. For example, one or more $\delta$ subunits and/or one or more additional subunits selected from the group of $\alpha$, $\beta$ and $\gamma$ including multiple copies of any particular subunit. The present invention requires that at least one copy of each of the $\alpha$, $\beta$ and $\gamma$ subunits are present. This composition is necessary because these subunits are necessary for a functional GABA$_A$ receptor which is capable of binding with benzodiazepines. Earlier attempts at producing stable cell lines were unsuccessful because it may not have been appreciated that at least one of each of these three subunit types are needed. In view of the teaching of the present invention, it can be hypothesized that receptors with less subunit types than those according to the present invention are lethal or detrimental to cells. As previous attempts demonstrate, only low levels of receptors can be produced by stable cells if the receptors consist of $\alpha$ and $\beta$ subunits only.

To produce any of the receptors within the scope of the present invention, the DNA encoding the various subunits is inserted into a 293 cell. According to the present invention, a DNA sequence encoding a subunit is inserted into an expression cassette, preferably in an expression plasmid. As used herein "expression cassette" refers to DNA sequences necessary for expression of coding sequence in eukaryotic cells. Expression sequences include a promoter, a transcription initiation region, and a termination region. Promoters can include both constitutive and inducible promoters. The necessary genetic elements for expression of a coding sequence in eukaryotic cells are well known as are the techniques to construct an expression cassette. In one embodiment of the present invention, the DNA sequences encoding various subunits used are inserted into plasmids, each subunit cDNA into a separate plasmid.

One such plasmid, pCDM8, is commercially available and preferred.

Several plasmids may be transfected into the HEK 293 cells simultaneously or in a step wise fashion. It is often useful to use selectable markers to distinguish cells that have taken up foreign DNA from cells that have not. Generally, selectable markers confer a phenotype on the cell that allow them to survive in the presence of compounds in the media which are lethal to cells that do not have the marker. For example, selectable markers include genes which confer antibiotic resistance such as resistance to kanamycin, ampicillin or neomycin. The use of selectable markers is widely known by those having ordinary skill in the art. With respect to the present invention, one or more selectable markers may be used. Plasmids containing a selectable marker gene may be co-transfected with plasmids containing DNA sequences that encode the various subunits. If all of the plasmids to be transfected are not transfected at the same time, a different transfection can be performed using a plasmid comprising a different selectable marker from that which was used in the first co-transfection.

$GABA_A$ receptors are gated channels which, upon binding to BAGA, allow chlorine ions to pass into the cell. In the presence of benzodiazepines. The $GABA_A$ receptor will allow GABA to open the channel and let more chlorine ion into the cell if the benzodiazepine is an agonist or less chlorine ions into the cell if the benzodiazepine is an inverse agonist. The amount of chlorine ions that pass through the $GABA_A$ receptor can be directly measured using the patch clamp assay. This assay measures the charge flow into and out of an electrode sealed on the surface of a cell. The flow of chlorine ions entering the cell is measured as a function of the current that leaves the cell to maintain electrical equilibrium within the cell as the gate opens. The patch assay is fully described in Hamill, O. P. et al., "Improved patch-clamp techniques for high-resolution current recording from cells and cell-free membrane patches"Pfluegers Arch. 391:85-100 (1981), which is incorporated herein by reference. Using the patch clamp assay, the effect a compound has on the receptor incorporated in the stable cell line can be determined. The range of sensitivity of the whole cell patch clamp assay is about 1000 pA and allows for the distinguishing of currents of between 2 and 5 pA.

EXAMPLES

EXAMPLE 1

One embodiment of the present invention is a group of cell lines established in a human embryonic kidney cell HEK 293 (transformed with adenovirus) which express a functional $GABA_A$ receptor-Cl$^-$ channel complex composed of rat $\alpha_1$, $\beta_2$, $\gamma_2$ subunits. The following references describe the GABA receptor subunit clones which have been used to produce transformed stable cell lines:

Rat $\alpha_1$-M. Khrestchalisky et al., Neuron vol. 3. p. 746-753, 1989;

Rat $\beta_2$-Ymer, S. et al., EMBO J. vol. 8, p. 1665-1670, 1989; and,

Rat $\gamma_2$-Shivers, B. D. et al., Neuron vol. 3, p. 329-337, 1989.

Four cell lines have been characterized, 2C-2C, 2C-1C, 1B-3B and 4A-3A, each having similar $\alpha_1$, $\beta_2$, $\gamma_2$ mRNA expression and GABA/benzodiazepine responses. Four separate plasmids PcdM8-$\alpha_1$, PcdM8-$\beta_2$, PcdM8-$\gamma_2$, PWL-Neo were transfected into HEK 293 cells and the transfected cells were subsequently selected with G418. The cDNAs encoding the respective subunits were cloned in vectors using the CMV immediate early promoter to drive transcription of the respective genes. The vector, pCDM8, is available from by Invitrogen Corporation, San Diego, Calif. 92121. The cDNA encoding the subunit was inserted into the plasmid by first digesting the plasmid with HindIII and PstI and ligating the cDNA at those sites in the plasmid. Plasmid DNA was prepared by the alkaline lysis procedure (Maniatis, T., E. F. Fritsch, and J. Sambrook, 1989, Molecular Cloning: A Laboratory Manual. Cold Spring Harbor Laboratory, Cold Spring Harbor, N.Y.) followed by two cycles of CsCl equilibrium density gradient centrifugation.

Transfection protocol used to transfect HEK 293 cells was adapted from Chen, C., and H. Okayama, 1987. High Efficiency Transformation of Mammalian Cells by Plasmid DNA. Mol. Cell. Biol. 7:2745-2752 (Chen-Okayama CaPO4 pH 6.95 technique). A stock solution of 2.5M $CaCl_2$ (Mallinckrodt) was prepared, filter sterilized through a 0.45-$\mu$m-pore-size nitrocellulose filter (Nalge) and stored at $-20°$ C. Then 2× Bes-buffered saline (2×BBS) containing 50 mM Bes (pH 6.95), 280 mM NaCl, and 1.5 mM $Na_2HPO_4$ was prepared, filter sterilized, and stored at $-20°$ C. N, N-bis(2-hydroxyethyl)-2-aminoetrane-sulfonic acid (BES) was obtained from Sigma. The pH was adjusted with HCl at room temperature. HEK 293 cells (American Type Culture Collection) were maintained in MEM(Bigco) supplemented with 10% Fetal Bovine Serum (Gibco), penicillin-streptomycin (Gibco), and glutamine (Gibco), in a 5% $CO_2$, 37° C. Forma Scientific Incubator.

Exponentially growing HEK 293 cells were removed with trypsin-EDTA, plated at a density of $1.5 \times 10^6$ cells per 10 cm plate, and incubated overnight at 5% $CO_2$, 37° C. in 10 mls of growth medium. For each 10 cm dish, 3.3 $\mu$g of each plasmid containing the individual rat $GABA_A$ receptor subunit ($\alpha_1$, $\beta_2$, $\gamma_2$) cDNA was used. For selection purposes 1 $\mu$g of a plasmid PWL-Neo (Stratagene) containing the aminoglycoside phosphotransferase (neo) gene driven by the thymidine kinase promoter was used per 10 cm dish containing $1 \times 10^6$ cells. Plasmid DNA was mixed with 50 $\mu$l of 2.5M $CaCl_2$ and brought to a final volume of 0.5 ml with water. This mixture was added to 0.5 ml of 2× BBS and incubated for 90 seconds at room temperature. This resulting calcium phosphate-DNA solution was added (1 ml volume) to the plate of cells, swirled gently, and incubated for 15-24 hours at 37° C. under 3% $CO_2$. The media was removed, the cells were rinsed two times with MEM media, and refed with fresh MEM+10% Fetal Bovine Serum. The cells were incubated for 48 hours at 37° C. under 5% $CO_2$.

Forty-eight hours after transfection the cells were trypsenized and split (1:8) into four plates per transfection. They were grown under selective pressure of growth media containing 1 mg/ml G418 sulfate (Gibco) at 1 mg/ml and grown for 2 weeks until colonies appeared. Selection of stable transformants took approximately 15-20 days. Colonies were selected into 24 well dishes and used after sufficient growth in G418 selective media to seed two 10 cm dishes. After sufficient growth in the 10 cm dishes, one was used to prepare total RNA; cells in the remaining dish were cryopreserved for possible future plating. The RNA for each clone was analyzed by Northern blotting and hybridization to the respective labeled $\alpha_1/\beta_2/\gamma_2$ cDNAs.

To determine the frequency of stable transformation, the cells were transfected, as described. At the point when the cells were split and plated under selective pressure (G418 sulfate), cells were also plated, in duplicate, at a density of $1-3\times 10^3$ cells per 10 cm plate. One set of plates was maintained in nonselective growth medium, while the duplicate plates were grown in growth media with G418 sulfate (1 mg/ml). Control plates were maintained in nonselective media 5-7 days; the colonies were then stained and counted. To determine the number of Neo+ transformants, cells were maintained under selective pressure for 2-3 weeks; the colonies were then stained and counted. The transformation efficiency is expressed as a % transformation. This is determined by dividing the number of Neo$^r$ colonies by the number of colonies grown in nonselective medium and multiplying the result by 100.

Clones which express all four gene products from the transfected plasmids were expanded to test for the expression of functional channels. These tests were carried out by patch-clamp electrophysiology of whole cells. The whole-cell configuration of patch clamp technique was used to record the GABA-mediated Cl-currents in human embryonic kidney cells transfected with GABA$_A$ receptor subunits. Patch pipettes were made of borosilicate glass with a resistance of 0.5 to 2 megohms. The cell was bathed in the buffer medium containing (mM) NaCl 135, KCl 5, MgCl2 1, CaCl2 1.8 and Hepes 5, pH 7.2. The pipette was filled with the solution containing (mM) CsCl140, EDTA 11, ATP 2, MgCl2 4 and Hepes 10, pH 7.3. The holding potential was $-60$ mV. The bathing solution containing 5 $\mu$M GABA with or without test drug was applied to the cell through a U-tube positioned about 100 microns away from the cell.

Cells that have a GABA response which can be potentiated by benzodiazepine binding are retained for cryopreservation and binding studies. The cell line 2C-2C was carried in continuous culture for 7 weeks or 12 passages and maintained a constant GABA/-GABA+Diazepam Cl$^-$ current ratio. It also has maintained the synthesis of mRNA for the $\alpha_1$, $\beta_2$, $\gamma_2$ inserted genes over this span of culture life time. The 2C—2C cells in culture appear to be epithelioid as are the parental cells. Cells of the cell line 2C—1C were also responsive to both GABA and Diazepam but grew in large islands in culture. Cells of the cell lines 1B-3B and 4A-3A, respectively, appear to resemble the 2C-2C cells in culture. All cell lines have an approximate doubling time of 15 hours.

EXAMPLE 2

Applying the same procedures described in Example 1, cell line C4-5 was constructed, using as starting materials the DNA sequences encoding rat $\alpha$3, $\beta$2, and $\gamma$2. The $\alpha$3 subunit is described in Pritchett, D. et al., J. Neurochemistry 54:1802-1804 (1990).

Cell lines A3-5, A3-6, A3-7, A3-13 and A3-14 express all three mRNAs $\alpha$3, $\beta$2 and $\gamma$2 and are derived from C4-5.

EXAMPLE 3

Applying the same procedures described in Example 1, cell line A6-36 was constructed, using as starting materials the DNA sequences encoding rat a5, b2, and g2. The a3 subunit is described in Lüddens, H. et al., Nature 346:648-651 (1990).

EXAMPLE 4

Following similar techniques as those described in Example 1, triple transfections were performed which generated cell line that contains rat subunits $\beta$2 and $\gamma$2 in addition to the Neo gene. This cell line was used as a starting material in a double transfection involving any one of the seven $\alpha$ subtypes and a second plasmid which contains the hygromycin marker. Cell lines H29 and H51 which contain $\alpha$3, $\beta$2 and $\gamma$2 were generated this way.

What is claimed is:

1. A stable transformed HEK 293 cell comprising a functional GABA$_A$ receptor comprising:
    a) a GABA$_A$ receptor $\alpha$ subunit;
    b) a GABA$_A$ receptor $\beta$ subunit; and,
    c) a GABA$_A$ receptor $\gamma$ subunit.

2. A stable transformed HEK 293 cell according to claim 1 further comprising a DNA sequence encoding a selectable marker.

3. A stable transformed HEK 293 cell according to claim 2 further comprising a DNA sequence encoding a second selectable marker.

4. A stable transformed HEK 293 cell according to claim 1 further comprising a GABA$_A$ receptor $\delta$ subunit.

5. A stable transformed HEK 293 cell according to claim 1 wherein said GABA$_A$ receptor $\alpha$ subunit is selected from the group consisting of: a GABA$_A$ receptor $\alpha_1$ subunit; a GABA$_A$ receptor $\alpha_3$ subunit; and, a GABA$_A$ receptor $\alpha_6$ subunit.

6. A stable transformed HEK 293 cell according to claim 1 wherein said GABA$_A$ receptor $\beta$ subunit is a GABA$_A$ receptor $\beta_2$ subunit.

7. A stable transformed HEK 293 cell according to claim 1 wherein said GABA$_A$ receptor $\gamma$ subunit is a GABA$_A$ receptor $\gamma_2$ subunit.

8. A stable transformed HEK 293 cell according to claim 1 wherein said GABA$_A$ receptor consists of;
    a) a GABA$_A$ receptor $\alpha_1$ subunit;
    b) a GABA$_A$ receptor $\beta_2$ subunit; and,
    c) a GABA$_A$ receptor $\gamma_2$ subunit.

9. A stable transformed HEK 293 cell according to claim 1 wherein said GABA$_A$ receptor consists of;
    a) a GABA$_A$ receptor $\alpha_3$ subunit;
    b) a GABA$_A$ receptor $\beta_2$ subunit; and,
    c) a GABA$_A$ receptor $\gamma_2$ subunit.

10. A stable transformed HEK 293 cell according to claim 1 wherein said GABA$_A$ receptor consists of;
    a) a GABA$_A$ receptor $\alpha_6$ subunit;
    b) a GABA$_A$ receptor $\beta_2$ subunit; and,
    c) a GABA$_A$ receptor $\gamma_2$ subunit.

11. A stable transformed HEK 293 cell comprising:
    a) a cDNA sequence encoding a GABA$_A$ receptor $\alpha$ subunit in an expression cassette;
    b) a cDNA sequence encoding a GABA$_A$ receptor $\beta$ subunit in an expression cassette; and
    c) a cDNA sequence encoding a GABA$_A$ receptor $\gamma$ subunit in an expression cassette;

12. A stable transformed HEK 293 cell according to claim 11 further comprising a DNA sequence encoding a selectable marker.

13. A stable transformed HEK 293 cell according to claim 12 further comprising a DNA sequence encoding a second selectable marker.

14. A stable transformed HEK 293 cell according to claim 11 further comprising a cDNA sequence encoding a GABA$_A$ receptor δ subunit in an expression cassette.

15. A stable transformed HEK 293 cell according to claim 11 wherein said GABA$_A$ receptor α subunit is selected from the group consisting of: a GABA$_A$ receptor $\alpha_1$ subunit; a GABA$_A$ receptor $\alpha_3$ subunit; and, a GABA$_A$ receptor $\alpha_6$ subunit.

16. A stable transformed HEK 293 cell according to claim 11 wherein said GABA$_A$ receptor β subunit is a GABA$_A$ receptor $\beta_2$ subunit.

17. A stable transformed HEK 293 cell according to claim 11 wherein said GABA$_A$ receptor γ subunit is a GABA$_A$ receptor $\gamma_2$ subunit.

18. A stable transformed HEK 293 cell according to claim 11 wherein:
 a) said cDNA sequence encoding a GABA$_A$ receptor α subunit in an expression cassette encodes GABA$_A$ receptor $\alpha_1$ subunit;
 b) said cDNA sequence encoding a GABA$_A$ receptor β subunit in an expression cassette encodes GABA$_A$ receptor $\beta_2$ subunit; and
 c) said cDNA sequence encoding a GABA$_A$ receptor γ subunit in an expression cassette encodes GABA$_A$ receptor $\gamma_2$ subunit.

19. A stable transformed HEK 293 cell according to claim 11 wherein:
 a) said cDNA sequence encoding a GABA$_A$ receptor α subunit in an expression cassette encodes GABA$_A$ receptor receptor $\alpha_3$ subunit;
 b) said cDNA sequence encoding a GABA$_A$ receptor β subunit in an expression cassette encodes GABA$_A$ receptor $\beta_2$ subunit; and
 c) said cDNA sequence encoding a GABA$_A$ receptor γ subunit in an expression cassette encodes GABA$_A$ receptor $\gamma_2$ subunit.

20. A stable transformed HEK 293 cell according to claim 11 wherein:
 a) said cDNA sequence encoding a GABA$_A$ receptor α subunit in an expression cassette encodes GABA$_A$ receptor $\alpha_6$ subunit;
 b) said cDNA sequence encoding a GABA$_A$ receptor receptor β subunit in an expression cassette encodes GABA$_A$ receptor $\beta_2$ subunit; and
 c) said cDNA sequence encoding a GABA$_A$ receptor γ subunit in an expression cassette encodes GABA$_A$ receptor $\gamma_2$ subunit.

* * * * *